March 13, 1962 L. L. BROOKS Plant Pat. 2,133

AZALEA PLANT

Filed June 30, 1959

INVENTOR
LENARD L. BROOKS

United States Patent Office

Plant Pat. 2,133
Patented Mar. 13, 1962

2,133
AZALEA PLANT

Lenard L. Brooks, Modesto, Calif.

Filed June 30, 1959, Ser. No. 824,141
1 Claim. (Cl. 47—60)

This specification describes a new and distinct variety of azalea plant, developed in the experimental section of my nursery at Modesto, California; this plant was produced by using pollen from an orange-red Kurume type azalea known as Vivid on a large flowered, double pink, Belgian Indica type azalea, name unknown to me. Neither of the parent varieties is patented.

I recognized novel characteristics in the original seedling plant that seemed to be a great improvement over other greenhouse forcing azaleas of a similar color; therefore, cuttings were taken for experimental asexual reproduction, and the plants thus produced carried forward all the novel characteristics of the original seedling plant. The original asexual reproduction by cuttings was carried out in the experimental section of my nursery at Modesto, California.

This variety is characterized particularly by its large, long lasting, orange-salmon double flowers; the bright waxed aspect of the heavy textured leaves; its habit of setting buds evenly and flowering evenly over the entire plant at one time; the ease with which it can be reproduced on its own roots and its high value as a greenhouse forcing or garden variety.

Referring now more specifically to the botanical details of this new and distinct variety of azalea plant, the following is a more detailed description thereof:

*Plant*

Form: Well branched, symmetrical, spreading.

Growing habit: Dense and bushy with an abundance of the dark green glossy leaves.

Blooming habit: Flowers evenly over the entire plant at one time when forced in the greenhouse or flowered naturally in the garden.

Blooming season: Plants growing in my experimental garden at Modesto, California, bloom naturally in March to April. Pinched at the right time and grown properly it forces easily for Christmas.

Foliage:

*Size.*—Maximum size of the mature foliage on young thrifty plants about 1 to 1⅜ inches wide and 2 to 2½ inches long, each plant having many smaller leaves. As the plants age the average size becomes smaller.

*Shape.*—Ovate, pointed.

*Aspect.*—Bright and smooth, but having many minute hairs on both sides.

*Texture.*—*Heavy.*

*Edge.*—Without serrations, some minute hairs.

*Ribs and veins.*—Normal.

Flower:

*Size.*—Three to four inches.

*Borne.*—One to three on each branch.

*Branch.*—Strong.

*Pedicel.*—½ to ⅝ inch long, very strong.

Figure 1:
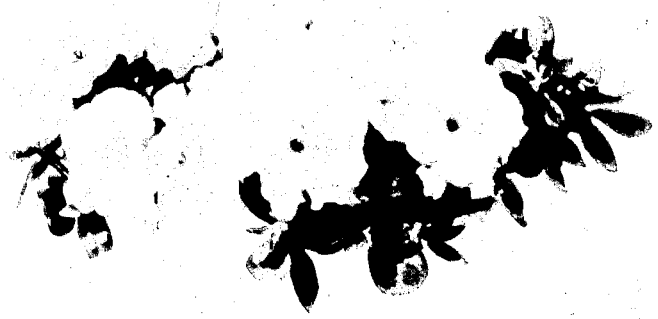
FIG. 1 shows a young plant in full flower, semi-forced.
Figure 2:
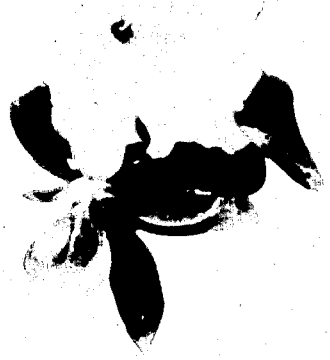
FIG. 2 shows flowers in about two thirds their normal size. This view shows in good detail the center structure of the flower, including the well developed pistil.

*Form.*—Double, Belgian Indica type, consisting of an outer section having five petals as found in the single azalea flower, and a varying number of smaller petals or petaloids in the center. As can be seen in both FIGS. 1 and 2, the center takes the form nearly like that of the inner hose in the hose-in-hose azalea flower. The center petals or pealoids are often antheriferous.

*Permanence.*—Long lasting, with little or no loss of color until the flower is ready to fall.

*Color.*—Salmon-orange. Plate 2–J–4, with prominent throat markings in a brownish-orchid shade. The reference to colors refers to Maerz and Paul Dictionary of Color.

Petals:

*Texture.*—Substantial.

*Appearance.*—Velvety inside and out.

*Shape.*—Broadly ovate.

*Arrangement.*—Normal for the Belgian Indica type azalea flower.

*Persistence.*—Remains firm until flower is ready to fall.

Reproductive organs:

*Stamens.*—Stamens rarely occur in this variety, but when they do appear, there are usually embryo petaloids attached at the base.

*Pollen.*—When pollen occurs, it is white. Another is brownish.

*Style.*—Style and stigma usually well developed, but sometimes both will be deformed. Color of style is similar to that of the petals. Stigma, brownish.

*Ovaries.*—Well developed.

*Comparison*

The azalea most similar to this new variety is the well known Paul Schame (not patented), but differs mainly in the following manner:

(a) The flowers are deeper in color; the substance is much better; the flowers stay on the plant much longer; retain their beauty for a much longer time and the center structure is better, having more and larger petals or petaloids.

(b) The leaves are larger, heavier textured and have a much brighter and smoother aspect.

(c) It flowers evenly over the entire plant at one time, while Paul Schame (not patented) blooms very unevenly and drops the first flowers before the last ones have opened.

Having thus disclosed my invention, I claim:

A new and distinct variety of azalea plant characterized particularly by its large long lasting double flowers in a distinctive shade of orange-salmon; the shining aspect of the large heavy textured leaves; the ease with which it can be reproduced on its own roots and its high value as a greenhouse forcing variety or as a garden variety for California or the lower South.

No references cited.